US012584064B2

(12) United States Patent
Christiansen et al.

(10) Patent No.: US 12,584,064 B2
(45) Date of Patent: Mar. 24, 2026

(54) ELECTROCHROMIC DEVICES AND COMPOSITIONS INCLUDING ANODIC COMPONENTS AS CATHODIC COMPONENT COUNTER-ANIONS

(71) Applicant: Vitro Flat Glass LLC, Cheswick, PA (US)

(72) Inventors: Dylan Thomas Christiansen, Pittsburgh, PA (US); Ivan Alexandrovich Sokol, Pittsburgh, PA (US)

(73) Assignee: Vitro Flat Glass LLC, Cheswick, PA (US)

( * ) Notice: Subject to any disclaimer, the term of this patent is extended or adjusted under 35 U.S.C. 154(b) by 356 days.

(21) Appl. No.: 18/134,057

(22) Filed: Apr. 13, 2023

(65) Prior Publication Data

US 2023/0340320 A1 Oct. 26, 2023

Related U.S. Application Data

(60) Provisional application No. 63/333,160, filed on Apr. 21, 2022.

(51) Int. Cl.

| | |
|---|---|
| ***C09K 9/02*** | (2006.01) |
| ***C07D 279/22*** | (2006.01) |
| ***G02F 1/15*** | (2019.01) |
| ***G02F 1/1516*** | (2019.01) |
| ***G02F 1/155*** | (2006.01) |

(52) U.S. Cl.

CPC .............. *C09K 9/02* (2013.01); *C07D 279/22* (2013.01); *G02F 1/15165* (2019.01); *G02F 1/155* (2013.01); *C09K 2211/1018* (2013.01); *G02F 2001/164* (2019.01)

(58) Field of Classification Search

CPC ............. G02F 1/1514; G02F 2001/164; G02F 2001/15145

See application file for complete search history.

(56) References Cited

U.S. PATENT DOCUMENTS

| | | | |
|---|---|---|---|
| 6,372,159 | B1 | 4/2002 | Berneth et al. |
| 6,545,793 | B2 | 4/2003 | Berneth et al. |
| 7,595,011 | B2 | 9/2009 | Kanouni et al. |
| 7,718,096 | B2 | 5/2010 | Yale et al. |
| 8,867,116 | B1 | 10/2014 | Kloeppner et al. |

(Continued)

FOREIGN PATENT DOCUMENTS

WO 2005026827 A2 3/2005

OTHER PUBLICATIONS

Kevan et al., "Applications of electron spin echo spectroscopy to location control of alkylphenothiazine derivatives in photoinduced charge separation across vesicles, micelles and reverse micelle interfaces", International Journal of Radiation Applications and Instrumentation. Part C. Radiation Physics and Chemistry, 1992, pp. 333-344, vol. 39, No. 1.

(Continued)

*Primary Examiner* — Lauren Nguyen

(74) *Attorney, Agent, or Firm* — The Webb Law Firm

(57) ABSTRACT

The present invention relates to electrochromic devices and compositions, in which the cathodic component has cationic charge and includes counter-anions, where each counter-anion of the cathodic component is an anodic component having an anion covalently bonded thereto.

17 Claims, 2 Drawing Sheets

(56) References Cited

U.S. PATENT DOCUMENTS

| | | | |
|---|---|---|---|
| 2002/0145790 A1 | 10/2002 | Berneth et al. | |
| 2006/0103911 A1 | 5/2006 | Baumann et al. | |
| 2019/0204703 A1* | 7/2019 | Giri | G02F 1/157 |

OTHER PUBLICATIONS

Jovanovski et al., "Tuning the Properties of Functional Pyrrolidinium Polymers by (Co)polymerization of Diallyldimethylammonium Ionic Liquids", Macromolecular Rapid Communications, 2010, pp. 1646-1651, vol. 31, No. 18.

Mecerreyes, "Polymeric ionic liquids: Broadening the properties and applications of polyelectrolytes", Progress in Polymer Science, 2011, pp. 1629-1648, vol. 36, No. 12.

Wang et al., "Preparation and characterization of gel polymer electrolytes using poly(ionic liquids) and high lithium salt concentration ionic liquids", Journal of Materials Chemistry A, 2017, Abstract, vol. 5, No. 45.

* cited by examiner

FIG. 2
(b)
1.2 V for 10 min
(a)
As Laminated
Vitro
Architectural Glass

ELECTROCHROMIC DEVICES AND COMPOSITIONS INCLUDING ANODIC COMPONENTS AS CATHODIC COMPONENT COUNTER-ANIONS

CROSS-REFERENCE TO RELATED APPLICATION

This application is entitled to and claims priority to U.S. Provisional Patent Application No. 63/333,160, which was filed on Apr. 21, 2022, the disclosure of which is incorporated herein by reference in its entirety.

FIELD

The present invention relates to electrochromic devices and compositions, in which the cathodic component has cationic charge and includes counter-anions, where each counter-anion of the cathodic component is an anodic component having an anion covalently bonded thereto.

BACKGROUND

Electrochromism involves a reversible change in a material's visible color and/or transmittance of visible light with the application of an electrical potential. The change in color and/or transmittance typically involves alternately cycled oxidized and reduced charge states. Generally, a material that generates a color while undergoing reduction is referred to as a cathodically-coloring electrochromic material; and a material that generates color while undergoing oxidation is referred to as an anodically-coloring electrochromic material.

Electrochromic devices typically include opposed electrodes (e.g., an anode and a cathode) having interposed there-between an electrochromic layer that is solution or gel-based. The kinetics of such electrochromic devices is typically governed primarily by mass transport of cathodic components and anodic components across and through the electrochromic layer. For purposes of charge conversion, the electrical currents of both electrodes are necessarily equal. If one of the components (cathodic or anodic component) moves or is transported more slowly through or across the electrochromic layer, typically a higher concentration of that component is required, and more particularly, a higher concentration gradient of the slower moving/transported component at the electrode interface (a higher interfacial concentration) is required to equalize the diffusion flux and maintain a given current. Adjusting and/or maintaining a higher concentration of the component having reduced mass transport can require additional preparation and/or manufacturing steps, and can result in inadvertent formulation errors. Mass transport imbalances can, in some instances, result in reduced durability of the electrochromic device, in particular if the slower mass transported active component is subject to over-oxidization or over-reduction at a particular electrode.

Factors that contribute to reduced mass transport of a component, and correspondingly mass transport imbalance as between the components, include, but are not limited to, reduced solubility of that component in the electrochromic layer and/or lack of a charge associated therewith. With some electrochromic devices, the cathodic component has a positive charge and has associated therewith counter-anions, while the anodic component has no charge associated therewith. The lack of charge associated with the anodic component can contribute to an undesirable mass transport imbalance relative to the cathodic component. In addition the counter-anions of the cathodic component can interfere with oxidation reactions at the anode.

It would be desirable to develop new electrochromic devices and compositions in which the active components thereof, and in particular, the cathodic and anodic components, provide improved mass transport balance. It would be further desirable that such newly developed electrochromic devices and compositions provide, or otherwise have associated therewith, improved durability, reduced costs of manufacture and/or operation, and/or improved efficiency of operation.

SUMMARY

In accordance with the present invention, there is provided an electrochromic device comprising: (a) a first substrate having a surface comprising a first transparent electrode layer; (b) a second substrate having a surface comprising a second transparent conductive electrode layer, where the first transparent electrode layer and the second transparent electrode layer are in opposing spaced opposition relative to each other; and (c) an electrochromic layer interposed between the first transparent electrically conductive electrode layer and the second transparent electrically conductive electrode layer. The electrochromic layer comprises: (i) an electrochromic material comprising a cathodic component having cationic charge, wherein the cathodic component further comprises counter-anions, wherein each counter-anion of the cathodic component is an anodic component having an anion covalently bonded thereto; (ii) an optional electrolyte; and (iii) a polymer matrix.

In accordance with the present invention, there is further provided an electrochromic composition comprising: (i) a cathodic component having cationic charge, wherein the cathodic component further comprises counter-anions, wherein each counter-anion of the cathodic component is an anodic component having an anion covalently bonded thereto; (ii) an optional electrolyte; (iii) a polymer thickener; and (iv) a solvent.

The features that characterize the present invention are pointed out with particularity in the claims, which are annexed to and form a part of this disclosure. These and other features of the invention, its operating advantages and the specific objects obtained by its use will be more fully understood from the following detailed description in which non-limiting embodiments of the invention are illustrated and described.

BRIEF DESCRIPTION OF THE DRAWINGS

In FIGS. 1 and 2 like characters refer to the same components and/or elements, as the case may be, unless otherwise stated.

DETAILED DESCRIPTION

Figure 1:
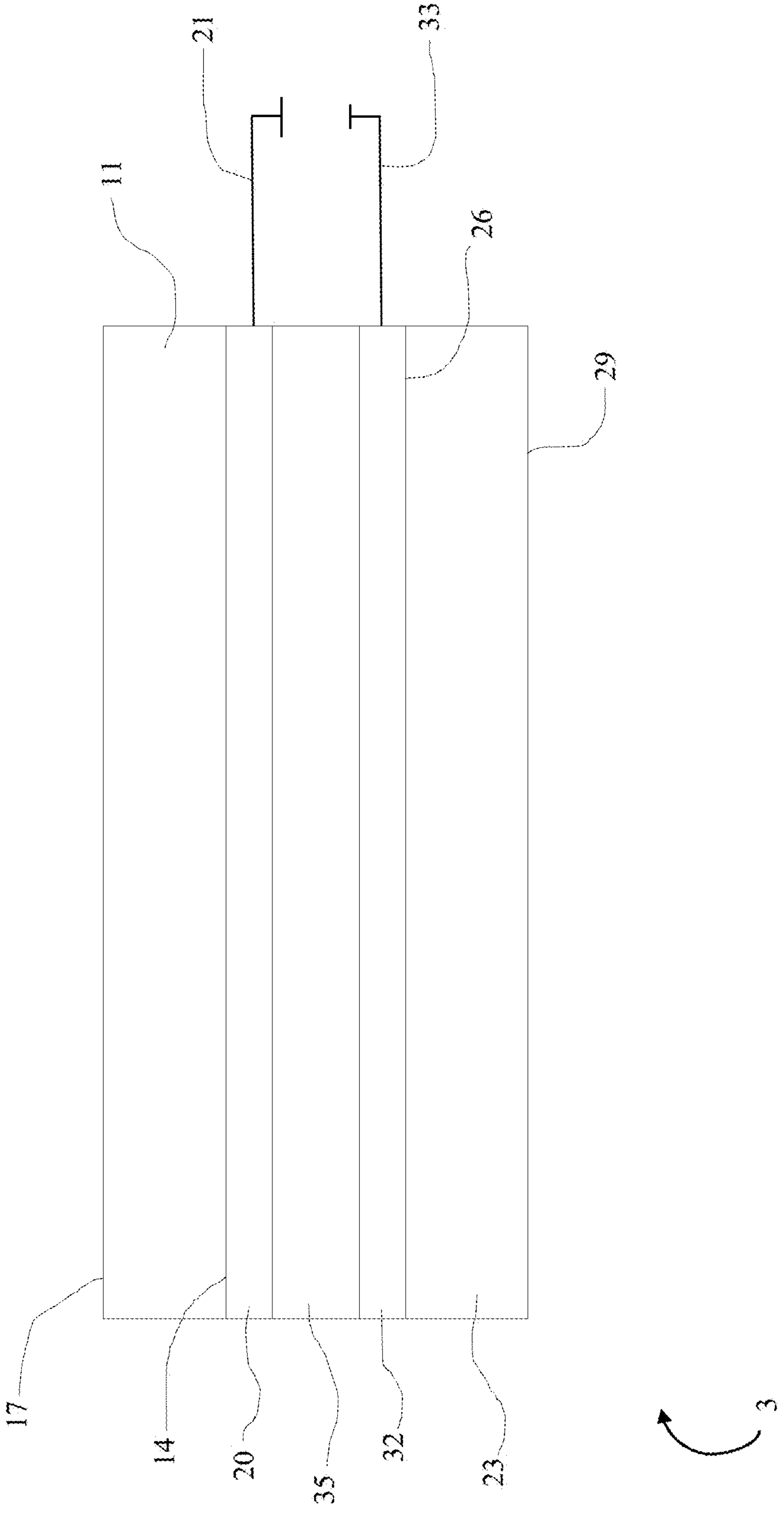
FIG. 1 is a representative side elevational sectional view of an electrochromic device according to the present invention.

As used herein, the articles "a," "an," and "the" include plural referents unless otherwise expressly and unequivocally limited to one referent.

Unless otherwise indicated, all ranges or ratios disclosed herein are to be understood to encompass any and all values, and subranges or subratios subsumed therein. For example, a stated range or ratio of "1 to 10" should be considered to include any and all values there-between (such as, 1, 2, 3, 4, 5, 6, 7, 8, 9, and 10), and subranges between (and inclusive of) the minimum value of 1 and the maximum value of 10; that is, all subranges or subratios beginning with a minimum value of 1 or more and ending with a maximum value of 10 or less, such as but not limited to, 1 to 6.1, 3.5 to 7.8, and 5.5 to 10.

As used herein, unless otherwise indicated, left-to-right representations of linking groups, such as divalent linking groups, are inclusive of other appropriate orientations, such as, but not limited to, right-to-left orientations. For purposes of non-limiting illustration, the left-to-right representation of the divalent linking group

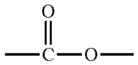

or equivalently —C(O)O—, is inclusive of the right-to-left representation thereof,

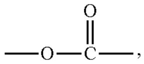, or equivalently —O(O)C— or —OC(O)—.

Other than in the operating examples, or where otherwise indicated, all numbers expressing quantities of ingredients, reaction conditions, and so forth used in the specification and claims are to be understood as modified in all instances by the term "about."

As used herein, molecular weight values of polymers, such as weight average molecular weights (Mw) and number average molecular weights (Mn), are determined by gel permeation chromatography using appropriate standards, such as polystyrene standards.

As used herein, polydispersity index (PDI) values represent a ratio of the weight average molecular weight (Mw) to the number average molecular weight (Mn) of the polymer (i.e., Mw/Mn).

As used herein, the term "polymer" means homopolymers (e.g., prepared from a single monomer species), copolymers (e.g., prepared from at least two monomer species), and graft polymers.

As used herein, the term "(meth)acrylate" and similar terms, such as "(meth)acrylic acid ester" means methacrylates and/or acrylates. As used herein, the term "(meth) acrylic acid" means methacrylic acid and/or acrylic acid.

As used herein, the term "electrochromic" and similar terms, such as "electrochromic compound" means having an absorption spectrum for at least visible radiation that varies in response to the application of an electric potential. Further, as used herein the term "electrochromic material" means any substance that is adapted to display electrochromic properties (such as, adapted to have an absorption spectrum for at least visible radiation that varies in response to an applied electric potential) and which includes at least one electrochromic compound.

As used herein, the term "electric potential" and related terms such as "electrical potential" means an electric potential that is capable of causing a response in a material, such as, but not limited to, transforming an electrochromic material from one form or state to another, as will be discussed in further detail herein.

As used herein to modify the term "state," the terms "first" and "second" are not intended to refer to any particular order or chronology, but instead refer to two different conditions or properties. For purposes of non-limiting illustration, the first state and the second state of an electrochromic compound, such as an anodically-coloring electrochromic compound, can differ with respect to at least one optical property, such as but not limited to the absorption of visible and/or UV radiation. Thus, according to various non-limiting embodiments disclosed herein, the anodically-coloring electrochromic compounds of the present invention can have a different absorption spectrum in each of the first and second state. For example, while not limiting herein, an anodically-coloring electrochromic compound can be clear in the first state and colored in the second state. Alternatively, an anodically-coloring electrochromic compound can have a first color in the first state and a second color in the second state.

As used herein the term "display" means the visible or machine-readable representation of information in words, numbers, symbols, designs or drawings. Non-limiting examples of display elements include screens, monitors, and security elements, such as security marks.

As used herein the term "window" means an aperture adapted to permit the transmission of radiation therethrough. Non-limiting examples of windows include automotive and aircraft transparencies, windshields, filters, shutters, and optical switches.

As used herein the term "mirror" means a surface that specularly reflects a large fraction of incident light.

As used herein, spatial or directional terms, such as "left", "right", "inner", "outer", "above", "below", and the like, relate to the invention as it is depicted in the drawing figures. It is to be understood, however, that the invention can assume various alternative orientations and, accordingly, such terms are not to be considered as limiting.

As used herein, the terms "formed over," "deposited over," "provided over," "applied over," residing over," or "positioned over," mean formed, deposited, provided, applied, residing, or positioned on but not necessarily in direct (or abutting) contact with the underlying element, or surface of the underlying element. For example, a layer "positioned over" a substrate does not preclude the presence of one or more other layers, coatings, or films of the same or different composition located between the positioned or formed layer and the substrate.

As used herein, the terms "interposed" and "interposed between," mean residing or positioned between, but not necessarily in direct (or abutting) contact with overlying and/or underlying elements, or surfaces thereof. For example, a layer "interposed between" a first substrate and a second substrate does not preclude the presence of one or more other layers, coatings, or films of the same or different composition located between the interposed layer and the first and/or second substrates.

All documents, such as but not limited to issued patents and patent applications, referred to herein, and unless otherwise indicated, are to be considered to be "incorporated by reference" in their entirety.

As used herein, recitations of "linear or branched" groups, such as linear or branched alkyl, are herein understood to include: a methylene group or a methyl group; groups that are linear, such as linear $C_2$-$C_{20}$ alkyl groups; and groups that are appropriately branched, such as branched $C_3$-$C_{20}$ alkyl groups.

The term "alkyl" as used herein means linear or branched, cyclic or acyclic $C_1$-$C_{25}$ alkyl. Linear or branched alkyl can include $C_1$-$C_{25}$ alkyl, such as $C_1$-$C_{20}$ alkyl, such as $C_2$-$C_{10}$ alkyl, such as $C_1$-$C_{12}$ alkyl, such as $C_1$-$C_6$ alkyl. Examples of alkyl groups from which the various alkyl groups of the present invention can be selected from, include, but are not limited to, those recited further herein. Alkyl groups can include "cycloalkyl" groups. The term "cycloalkyl" as used herein means groups that are appropriately cyclic, such as, but not limited to, $C_3$-$C_{12}$ cycloalkyl (including, but not limited to, cyclic $C_3$-$C_{10}$ alkyl, or cyclic $C_5$-$C_7$ alkyl) groups. Examples of cycloalkyl groups include, but are not limited to, those recited further herein. The term "cycloalkyl" as used herein also includes: bridged ring polycycloalkyl groups (or bridged ring polycyclic alkyl groups), such as, but not limited to, bicyclo[2.2.1]heptyl (or norbornyl) and bicyclo[2.2.2]octyl; and fused ring polycycloalkyl groups (or fused ring polycyclic alkyl groups), such as, but not limited to, octahydro-1H-indenyl, and decahydronaphthalenyl.

The term "heterocycloalkyl" as used herein means groups that are appropriately cyclic, such as, but not limited to, $C_2$-$C_{12}$ heterocycloalkyl groups, such as $C_2$-$C_{10}$ heterocycloalkyl groups, such as $C_5$-$C_7$ heterocycloalkyl groups, and which have at least one hetero atom in the cyclic ring, such as, but not limited to, O, S, N, P, and combinations thereof. Examples of heterocycloalkyl groups include, but are not limited to, imidazolyl, tetrahydrofuranyl, tetrahydropyranyl and piperidinyl. The term "heterocycloalkyl" as used herein also includes: bridged ring polycyclic heterocycloalkyl groups, such as, but not limited to, 7-oxabicyclo[2.2.1]heptanyl; and fused ring polycyclic heterocycloalkyl groups, such as, but not limited to, octahydrocyclopenta[b]pyranyl, and octahydro-1H-isochromenyl.

The descriptions, classes, and examples provided herein with regard to alkyl groups, cycloalkyl groups, heterocycloalkyl groups, haloalkyl groups, and the like, are also applicable to alkane groups, cycloalkane groups, heterocycloalkane groups, haloalkane groups, etc., such as, but not limited to, polyvalent alkane groups, such as polyvalent alkane linking groups, such as divalent alkane linking groups.

As used herein, the term "aryl" and related terms, such as "aryl group", means an aromatic cyclic monovalent hydrocarbon radical. As used herein, the term "aromatic" and related terms, such as "aromatic group," means a cyclic conjugated hydrocarbon having stability (due to delocalization of pi-electrons) that is significantly greater than that of a hypothetical localized structure. Examples of aryl groups include $C_6$-$C_{14}$ aryl groups, such as, but not limited to, phenyl, naphthyl, phenanthryl, and anthracenyl.

The term "heteroaryl", as used herein, includes, but is not limited to, $C_3$-$C_{18}$ heteroaryl, such as, but not limited to, $C_3$-$C_{10}$ heteroaryl (including fused ring polycyclic heteroaryl groups) and means an aryl group having at least one hetero atom in the aromatic ring, or in at least one aromatic ring in the case of a fused ring polycyclic heteroaryl group. Examples of heteroaryl groups include, but are not limited to, furanyl, pyranyl, pyridinyl, quinolinyl, isoquinolinyl, and pyrimidinyl.

The term "aralkyl", as used herein, includes, but is not limited to, $C_6$-$C_{24}$ aralkyl, such as, but not limited to, $C_6$-$C_{10}$ aralkyl, and means an alkyl group substituted with an aryl group. Examples of aralkyl groups include, but are not limited to, benzyl and phenethyl.

Representative alkyl groups include, but are not limited to, methyl, ethyl, propyl, isopropyl, butyl, isobutyl, sec-butyl, tert-butyl, pentyl, neopentyl, hexyl, heptyl, octyl, nonyl and decyl. Representative alkenyl groups include, but are not limited to, vinyl, allyl, and propenyl. Representative alkynyl groups include, but are not limited to, ethynyl, 1-propynyl, 2-propynyl, 1-butynyl, and 2-butynyl. Representative cycloalkyl groups include, but are not limited to, cyclopropyl, cyclobutyl, cyclopentyl, cyclohexyl, and cyclooctyl.

The term "nitrogen-containing heterocycle," such as "nitrogen-containing heterocycle group" or nitrogen-containing heterocycle substituent", as used herein, includes, but is not limited to, a nitrogen-containing ring in which the nitrogen-containing ring is bonded through a ring nitrogen. Examples of nitrogen-containing heterocycles include, but are not limited to, aliphatic cyclic aminos (or cycloaliphatic aminos), such as morpholino, piperidino, pyrrolidino, and decahydroisoquinolino; and heteroaromatics, such as imidazole, pyrrole, indole, and carbazole.

As used herein, recitations of "substituted" group, means a group including, but not limited to, alkyl group, cycloalkyl group, heterocycloalkyl group, aryl group, and/or heteroaryl group, in which at least one hydrogen thereof has been replaced or substituted with a group or "substituent" that is other than hydrogen, such as, but not limited to: alkoxy groups; halo groups (e.g., F, Cl, I, and Br); hydroxyl groups; thiol groups; alkylthio groups; arylthio groups; ketone groups; aldehyde groups; carboxylic ester groups; carboxylic acid groups; phosphoric acid groups; phosphoric acid ester groups; sulfonic acid groups; sulfonic acid ester groups; nitro groups; cyano groups; alkyl groups; alkenyl groups; alkynyl groups; haloalkyl groups; perhaloalkyl groups; heterocycloalkyl groups; aryl groups (including alkaryl groups, including hydroxyl substituted aryl, such as phenol, and including poly-fused-ring aryl); aralkyl groups; heteroaryl groups (including poly-fused-ring heteroaryl groups); amino groups, such as —$N(R^{11'})(R^{12'})$ where $R^{11'}$ and $R^{12'}$ are each independently selected from, for example, hydrogen, alkyl, heterocycloalkyl, aryl, or heteroaryl; carboxylate groups; siloxane groups; alkoxysilane groups; polysiloxane groups; amide groups; carbamate groups; carbonate groups; urea groups; trialkylsilyl groups; nitrogen-containing heterocycles; or combinations thereof, including those classes and examples as described further herein. In accordance with some embodiments of the present invention, the substituents of a substituted group are more particularly recited.

As used herein, the term "halo" and related terms, such as "halo group," "halo substituent," "halogen group," and "halogen substituent," means a single bonded halogen group, such as —F, —Cl, —Br, and —I.

As used herein, recitations of "halo substituted" and related terms (such as, but not limited to, haloalkyl groups, haloalkenyl groups, haloalkynyl groups, haloaryl groups, and halo-heteroaryl groups) means a group in which at least one, and up to and including all of the available hydrogen groups thereof is substituted with a halo group, such as, but not limited to F, Cl or Br. The term "halo-substituted" is inclusive of "perhalo-substituted." As used herein, the term perhalo-substituted group and related terms (such as, but not limited to, perhaloalkyl groups, perhaloalkenyl groups, perhaloalkynyl groups, perhaloaryl groups or perhalo-heteroaryl groups) means a group in which all of the available hydrogen groups thereof are substituted with a halo group.

For purposes of non-limiting illustration: perhalomethyl is $—CX_3$; and perhalophenyl is $—C_6X_5$, where X represents one or more halo groups, such as, but not limited to F, Cl, Br, or I.

As used herein, "at least one of" is synonymous with "one or more of," whether the elements are listed conjunctively or disjunctively. For example, the phrases "at least one of A, B, and C" and "at least one of A, B, or C" each mean any one of A, B, or C, or any combination of any two or more of A, B, or C. For example, A alone; or B alone; or C alone; or A and B; or A and C; or B and C; or all of A, B, and C.

As used herein, "selected from" is synonymous with "chosen from" whether the elements are listed conjunctively or disjunctively. Further, the phrases "selected from A, B, and C" and "selected from A, B, or C" each mean any one of A, B, or C, or any combination of any two or more of A, B, or C. For example, A alone; or B alone; or C alone; or A and B; or A and C; or B and C; or all of A, B, and C.

The discussion of the present invention herein may describe certain features as being "particularly" or "preferably" within certain limitations (e.g., "preferably," "more preferably," or "even more preferably," within certain limitations). It is to be understood that the invention is not limited to or by such particular or preferred limitations, but encompasses the entire scope of the disclosure.

As used herein, and in accordance with some embodiments, the term "ketone" such as with regard to groups, and substituents of various groups, of the compounds and components of the present invention, and related terms, such as "ketone group" and "ketone substituent," includes a material represented by —C(O)R, where R is selected from those groups as described below, other than hydrogen.

As used herein, and in accordance with some embodiments, the term "carboxylic acid" such as with regard to groups, and substituents of various groups, of the compounds and components of the present invention, and related terms, such as "carboxylic acid group" and "carboxylic acid substituent" includes a material represented by —C(O)OH.

As used herein, and in accordance with some embodiments, the term "ester" such as with regard to groups, and substituents of various groups, of the compounds and components of the present invention, and related terms, such as "ester group" and "ester substituent" means a carboxylic acid ester group represented by —C(O)OR, where R is selected from those groups as described below, other than hydrogen.

As used herein, and in accordance with some embodiments, the term "carboxylate" such as with regard to groups, and substituents of various groups, of the compounds and components of the present invention, and related terms, such as "carboxylate group" and "carboxylate substituent," includes a material represented by —OC(O)R, where R is selected from those groups as described below.

As used herein, and in accordance with some embodiments, the term "amide" such as with regard to groups, and substituents of various groups, of the compounds and components of the present invention, and related terms, such as "amide group" and "amide substituent" includes a material represented by —(O)N(R)(R) or —N(R)C(O)R, where each R is independently selected from those groups as described below.

As used herein, and in accordance with some embodiments, the term "carbonate" such as with regard to groups, and substituents of various groups, of the compounds and components of the present invention, and related terms, such as "carbonate group" and "carbonate substituent" includes a material represented by —OC(O)OR, where R is selected from those groups as described below, other than hydrogen.

As used herein, and in accordance with some embodiments, the term "carbamate" such as with regard to groups, and substituents of various groups, of the compounds and components of the present invention, and related terms, such as "carbamate group" and "carbamate substituent" includes a material represented by —OC(O)N(R)(H) or —N(H)C(O)OR, where R in each case is independently selected from those groups as described below, other than hydrogen.

As used herein, and in accordance with some embodiments, the term "urea" such as with regard to groups, and substituents of various groups, of the compounds and components of the present invention, and related terms, such as "urea group" and "urea substituent" includes a material represented by —N(R)C(O)N(R)(R), where each R is independently selected from those groups as described below.

As used herein, and in accordance with some embodiments, the term "siloxy" such as with regard to groups, and substituents of various groups, of the compounds and components of the present invention, and related terms, such as "siloxy group" and "siloxy substituent" includes a material represented by $—O—Si(R)_3$ where each R is independently selected from those groups as described below, other than hydrogen.

As used herein, and in accordance with some embodiments, the term "alkoxysilane" such as with regard to groups, and substituents of various groups, of the compounds and components of the present invention, and related terms, such as "alkoxysilane group" and alkoxysilane substituent" includes a material represented by $—Si(OR'')_w(R)_t$, where w is 1 to 3 and t is 0 to 2, provided the sum of w and t is 3; R'' for each w is independently selected from alkyl; and R for each t is independently selected from those groups as described below, other than hydrogen.

As used herein, and in accordance with some embodiments, the term "polysiloxane" such as with regard to groups, and substituents of various groups, of the compounds and components of the present invention, and related terms, such as "polysiloxane group" and "polysiloxane substituent", includes a material represented by the following Formula (A):

(A)

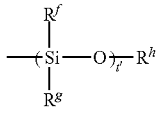

With reference to Formula (A): t' is greater than or equal to 2, such as from 2 to 200; $R^f$ and $R^g$ for each t' are each independently selected from a group R as described below, other than hydrogen; and $R^h$ is independently a group R as described below.

Unless otherwise stated, each R group of each of the above described ketone, ester (carboxylic acid ester), carboxylate, amide, carbonate, carbamate, urea, siloxane, alkoxysilane groups, and polysiloxane groups, is in each case independently selected from hydrogen, alkyl, haloalkyl, perhaloalkyl, cycloalkyl, heterocycloalkyl, aryl, heteroaryl, and combinations thereof (including those classes and examples thereof as recited previously herein).

In accordance with the present invention, the electrochromic material (of the electrochromic layer of the electrochromic device) includes a cathodic component having cationic charge, where the cathodic component further includes counter-anions, and where each counter-anion of the cathodic component is an anodic component having an anion covalently bonded thereto. With some further embodiments, the anodic component having an anion covalently bonded thereto is an anodically-coloring electrochromic compound having an anion covalently bonded thereto.

Reference herein to counter-ions (such as counter-cations and/or counter-anions) of a component, with some embodiments, means the counter-ions of the component when it is prepared separately from and/or prior to combining with the electrochromic layer and/or electrochromic composition of the present invention.

With some embodiments, (i) the cathodic component having cationic charge and (ii) the anodic component having an anion covalently bonded thereto, together have a net neutral charge. As used herein, the term "net neutral charge" with regard to the cathodic component having cationic charge and the anodic component having an anion covalently bonded thereto, means that the sum of the cationic charge (+) of the cathodic component, and the sum of the anionic charge (−) of the anodic component having an anion covalently bonded thereto, are equal to each other (or have the same absolute value). In accordance with some embodiments, the cathodic component having cationic charge is free of any other or further counter-anions, other than the anodic component having an anion covalently bonded thereto. Correspondingly, and with some embodiments, the anodic component having an anion covalently bonded thereto is free of any other or further counter-cations, other than the cathodic component having cationic charge.

In accordance with some embodiments of the present invention, the anodic component having an anion covalently bonded thereto is selected from an anodic component represented by at least one of the following Formula (I) or Formula (II), Formula (I)

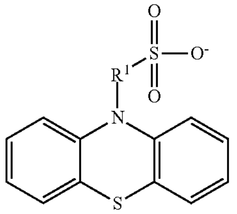

Formula (II)

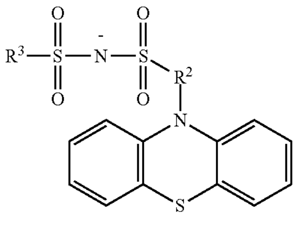

With reference to Formula (I), $R^1$ is selected from divalent linear or branched alkane linking group.

With reference to Formula (II), $R^2$ is selected from divalent linear or branched alkane linking group, and $R^3$ is selected from fluorine, linear or branched fluorinated alkyl, or linear or branched perfluorinated alkyl.

With further reference to Formula (I), and in accordance with some embodiments of the present invention, $R^1$ is selected from divalent linear or branched $C_1$-$C_{10}$ alkane linking group.

With reference to Formula (II), and in accordance with some embodiments of the present invention, $R^2$ is selected from divalent linear or branched $C_1$-$C_{10}$ alkane linking group, and $R^3$ is selected from fluorine, linear or branched $C_1$-$C_{10}$ fluorinated alkyl, or linear or branched $C_1$-$C_{10}$ perfluorinated alkyl.

With further reference to Formula (I), $R^1$ is selected from a divalent linear or branched $C_1$-$C_5$ alkane linking group. With some embodiments, $R^1$ is selected from divalent methane, divalent ethane, divalent linear or branched propane, divalent linear or branched butane, and divalent linear or branched pentane.

With further reference to Formula (II), $R^2$ is selected from divalent linear or branched $C_1$-$C_5$ alkyl, and $R^3$ is selected from linear or branched $C_1$-$C_5$ perfluorinated alkyl. With some embodiments, $R^2$ is selected from divalent methane, divalent ethane, divalent linear or branched propane, divalent linear or branched butane, and divalent linear or branched pentane. With some further embodiments, $R^3$ of Formula (II) is selected from fluorinated or perfluorinated versions or derivatives of methyl, ethyl, linear or branched propyl, linear or branched butyl, and linear or branched pentyl.

With some embodiments of the present invention, anodic components having anions covalently bonded thereto, such as represented by Formula (I) and Formula (II) can be prepared in accordance with the non-limiting synthetic descriptions provided in the examples further herein.

The cathodic component having cationic charge, with some embodiments of the present invention, includes at least one of a 1,1'-disubstituted-4,4'-dipyridinium cation represented by the following Formula (III), and/or a 1,1-(alkane-alpha, omega-diyl)-bis-(1'-substituted-4,4'-dipyridinium) cation represented by the following Formula (VI):

Formula (III)

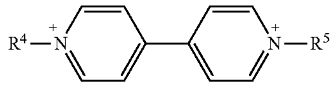

Formula (IV)

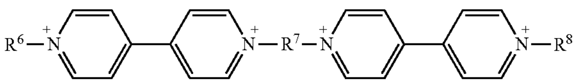

With reference to Formula (III), $R^4$ and $R^5$ are each independently selected from linear or branched $C_1$-$C_{10}$ alkyl, unsubstituted $C_3$-$C_7$ cycloalkyl, substituted $C_3$-$C_7$ cycloalkyl, unsubstituted aryl, and substituted aryl.

With reference to Formula (IV), and in accordance with some embodiments, $R^6$ and $R^8$ are each independently selected from linear or branched $C_1$-$C_{10}$ alkyl, unsubstituted $C_3$-$C_7$ cycloalkyl, substituted $C_3$-$C_7$ cycloalkyl, unsubstituted aryl, and substituted aryl, and $R^7$ is selected from divalent linear or branched $C_1$-$C_{10}$ alkane linking group.

The aryl groups of the unsubstituted aryl groups and substituted aryl groups, from which $R^4$ and $R^5$ of Formula (III), and $R^6$ and $R^8$ of Formula (IV), can each be independently selected, include those aryl groups as recited previously herein, such as, but not limited to, phenyl, naphthyl, phenanthryl, and anthracenyl. The cycloalkyl groups of the unsubstituted cycloalkyl groups and substituted cycloalkyl groups, from which $R^4$ and $R^5$ of Formula (III), and $R^6$ and $R^8$ of Formula (IV), can each be independently selected, include those cycloalkyl groups as recited previously herein, such as, but not limited to, cyclopentyl, cyclohexyl, and cycloheptyl.

The substituents of the substituted cycloalkyl and substituted aryl groups, from which $R^4$ and $R^5$ of Formula (III), and $R^6$ and $R^8$ of Formula (IV), can each be independently selected, include those substituents as recited previously herein. With some embodiments, each substituent of the substituted cycloakyl and substituted aryl groups, from which $R^4$ and $R^5$ of Formula (III), and $R^6$ and $R^8$ of Formula (IV), can each be independently selected, are each independently selected from: alkoxy groups; halo groups (e.g., F, Cl, I, and Br); hydroxyl groups; thiol groups; alkylthio groups; arylthio groups; ketone groups; aldehyde groups; haloalkyl groups; perhaloalkyl groups; heterocycloalkyl groups; aryl groups; aralkyl groups (such as, benzyl groups); heteroaryl groups; and amino groups.

The linear or branched alkyl groups from which $R^4$ and $R^5$ of Formula (III), and from which $R^6$ and $R^8$ of Formula (IV), can each be independently selected, include those classes and examples of alkyl groups as recited previously herein, such as, but not limited to, methyl, ethyl, linear or branched propyl, linear or branched butyl, linear or branched pentyl, linear or branched hexyl, and linear or branched heptyl.

With further reference to Formula (III), and in accordance with some embodiments of the present invention, $R^4$ and $R^5$ are each independently selected from linear or branched $C_1$-$C_4$ alkyl, unsubstituted phenyl, and substituted phenyl.

With further reference to Formula (IV), and in accordance with some embodiments of the present invention, $R^6$ and $R^8$ are each independently selected from linear or branched $C_1$-$C_4$ alkyl, unsubstituted phenyl, and substituted phenyl, and $R^7$ is selected from divalent linear or branched $C_1$-$C_8$ alkane linking group. With some further embodiments, $R^7$ of Formula (IV) is a divalent linear or branched $C_1$-$C_5$ alkane linking group, such as a divalent linear or branched $C_3$-$C_5$ alkane linking group.

With some embodiments, each substituent of the substituted phenyl groups, from which $R^4$ and $R^5$ of Formula (III), and from which $R^6$ and $R^8$ of Formula (IV), can each be independently selected, are each independently selected from: alkoxy groups; halo groups (e.g., F, Cl, I, and Br); hydroxyl groups; thiol groups; alkylthio groups; arylthio groups; ketone groups; aldehyde groups; haloalkyl groups; perhaloalkyl groups; aryl groups; and aralkyl groups (such as, benzyl groups).

With some embodiments of the present invention, and for purposes of non-limiting illustration, the cathodic component having cationic charge, such as represented by Formula (III), and the anodic component having an anion covalently bonded thereto (such as represented by Formula (I) or Formula (II)), can be represented by the following Formula (V), Formula (V)

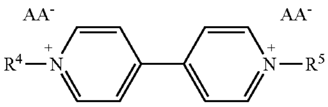

With reference to Formula (V), $R^4$ and $R^5$ are each independently as described previously herein with reference to Formula (III), and each $AA^-$ (anodic anion) is independently selected from an anodic component having an anion covalently bonded thereto represented by Formula (I) or Formula (II).

With some embodiments of the present invention, and for purposes of non-limiting illustration, the cathodic component having cationic charge, such as represented by Formula (IV), and the anodic component having an anion covalently bonded thereto (such as represented by Formula (I) or Formula (II)), can be represented by the following Formula (VI), Formula (VI)

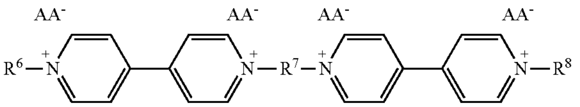

With reference to Formula (VI), $R^6$, $R^8$, and $R^7$ are each independently as described previously herein with reference to Formula (IV), and each $AA^-$ (anodic anion) is independently selected from an anodic component having an anion covalently bonded thereto represented by Formula (I) or Formula (II).

The neutral charge combination of the cathodic component having cationic charge and the anodic component having an anion covalently bonded thereto, can be prepared in accordance with the non-limiting preparatory description provided in the examples further herein.

In accordance with some embodiments of the present invention, the cathodic component having cationic charge is present in the electrochromic layer in an amount of from 0.25 percent by weight to 6.25 percent by weight, or from 0.5 percent by weight to 5 percent by weight, or from 1 percent by weight to 3 percent by weight, the percent weights in each case being based on the total weight of the electrochromic layer.

The anodic component having an anion covalently bonded thereto, with some embodiments, is present in the electrochromic layer in an amount of from 0.25 percent by weight to 6.25 percent by weight, or from 0.5 percent by weight to 5 percent by weight, or from 1 percent by weight to 3 percent by weight, the percent weights in each case being based on the total weight of the electrochromic layer.

In accordance with some embodiments, in addition to the anodic component anion having an anion covalently bonded thereto, such as represented by Formula (I) and/or Formula (II), the anodic component of the electrochromic layer includes one or more further anodic electrochromic compounds, such as, but not limited to: ferrocene and/or ferrocene derivatives (in which at least one cyclopentadienyl ring thereof is substituted with at least one substituent, including those substituents recited previously herein); 5,10-dihydro-5,10-di(linear or branched $C_1$-$C_{10}$ alkyl)phenazine, such as 5,10-dihydro-5,10-dimethylphenazine; N-substitutedphenoxazine, such as N-phenylphenoxazine; and combinations thereof. With some embodiments, the further anodic electrochromic component is present in an amount of 1 percent by weight to 50 percent by weight, of from 1 percent by weight to 25 percent by weight, or from 1 percent by weight to 10 percent by weight, or from 1 percent by weight to 5 percent by weight, the percent weights each being based on the total weight of the anodic component having an anion covalently bonded thereto and the further anodic electrochromic component. In accordance with some embodiments, when a further anodic component in present (in addition to the anodic component anion having an anion covalently bonded thereto) a further cathodic component (or further appropriate amount of cathodic component) can also be present. The further cathodic component, with some embodiments, comprises one or more cathodic components represented by Formulas (III) and/or (IV).

With some embodiments of the present invention, the electrochromic layer of the electrochromic device of the present invention, includes an electrolyte. The electrolyte includes, with some embodiments, at least one electrolyte anion and at least one electrolyte cation. The electrolyte of the electrochromic layer includes, with some embodiments, an equal number of electrolyte anions and electrolyte cations, and correspondingly has a net neutral charge.

With some embodiments, the electrolyte of the electrochromic layer includes at least one electrolyte anion, where each electrolyte anion is independently selected from chloride, hexafluorophosphate, and bis(perfluoro(linear or branched $C_1$-$C_6$ alkysulfonyl)imide. With some further embodiments, the electrolyte of the electrochromic layer includes at least one electrolyte cation, where each electrolyte cation is independently selected from: sodium; potassium; lithium; ammonium cations, such as, tetra(linear or branched $C_1$-$C_6$)ammonium, and tri($C_5$-$C_8$ cycloalkyl)-(linear or branched $C_1$-$C_6$ alkyl)ammonium; 1-(linear or branched $C_1$-$C_6$ alkyl)-3-(linear or branched $C_1$-$C_6$ alkyl) imidazolium; 1-(linear or branched $C_1$-$C_6$ alkyl)-1-(linear or branched $C_1$-$C_6$ alkyl)pyrrolidinium; 1-(linear or branched $C_1$-$C_6$ alkyl)-1-(linear or branched $C_1$-$C_6$ alkyl)piperidinium; or phosphonium cations, such as, but not limited to tetra(linear or branched $C_1$-$C_6$ alkyl)phosphonium, or tri($C_5$-$C_8$ cycloalkyl)-(linear or branched $C_1$-$C_6$ alkyl)phosphonium.

The electrolyte of the electrochromic layer, with some embodiments includes: at least one electrolyte anion, where each electrolyte anion is independently selected from bis (perfluoro(linear or branched $C_1$-$C_6$ alkysulfonyl)imide; and at least one electrolyte cation, wherein each electrolyte cation is independently selected from 1-(linear or branched $C_1$-$C_6$ alkyl)-3-(linear or branched $C_1$-$C_6$ alkyl)imidazolium, 1-(linear or branched $C_1$-$C_6$ alkyl)-1-(linear or branched $C_1$-$C_6$ alkyl)pyrrolidinium, or 1-(linear or branched $C_1$-$C_6$ alkyl)-1-(linear or branched $C_1$-$C_6$ alkyl) piperidinium.

The electrolyte of the electrochromic layer, with some further embodiments includes: at least one electrolyte anion, where each electrolyte anion is bis(trifluromethylsulfonyl) imide; and at least one electrolyte cation, where each electrolyte cation is independently selected from 1-ethyl-3-methylimidazolium, 1-butyl-3-methylimidazolium, 1-methyl-1-butylpyrrolidinium, and 1-methyl-1-propylpiperidinium.

The electrolyte, with some embodiments, is present in the electrochromic layer in an amount of from 1 percent by weight to 75 percent by weight, or from 5 percent by weight to 50 percent by weight, or from 10 percent by weight to 30 percent by weight, the percent weights in each case being based on the total weight of the electrochromic layer.

In accordance with some further embodiments, the electrochromic layer of the present invention includes a solvent. With some additional embodiments, the solvent is present, in the electrochromic layer, alternatively to or in addition to the electrolyte. The solvent can, with some embodiments, include at least one of ethylene carbonate, propylene carbonate, gamma-butyrolactone, gamma-valerolactone, N-methylpyrrolidone, polyethylene glycol, carboxylic acid esters of polyethylene glycol, sulfolane, alpha, omega-($C_2$-$C_8$)dinitriles, or di(linear or branched $C_1$-$C_8$)acetamides. While not intending to be bound by any theory, and in accordance with some embodiments, it is believed that the solvent acts, at least in part, as a plasticizer within (or plasticizes) the electrochromic layer. The solvent, with some embodiments, is present in the electrochromic layer in an amount of from 10 to 75 percent by weight, or from 20 to 60 percent by weight, the percent weights in each case being based on the total weight of the electrochromic layer and the solvent.

The electrochromic layer, of the electrochromic devices of the present invention, includes a polymer matrix. The polymer matrix includes at least one polymer. The polymer matrix, with some embodiments, is a gelled polymer matrix, a crosslinked polymer matrix, and/or a thermoplastic polymer matrix.

With some embodiments, the polymer matrix includes a polymer, where the polymer includes at least one of poly ((meth)acrylonitrile), poly(vinylidene fluoride), poly(vinylidene fluoride-co-perfluoro(linear or branched $C_1$-$C_6$ alkylene)), or poly((linear or branched $C_1$-$C_8$ alkyl)(meth) acrylate).

The polymer matrix, with some embodiments, is present in the electrochromic layer in an amount of from 5 percent by weight to 80 percent by weight, or from 10 percent by weight to 60 percent by weight, or from 15 percent by weight to 50 percent by weight, the percent weights in each case being based on the total weight of the electrochromic layer.

The electrochromic layer of the electrochromic devices of the present invention can, with some embodiments, further include one or more art-recognized optional additives, such as, but not limited to, thermal stabilizers, UV stabilizers, rheology modifiers, static coloring agents (such as static tints and/or static dyes), kinetic additives (that accelerate electrode reaction) and combinations thereof. A non-limiting class of art-recognized thermal stabilizers are phenols, such as 2,6-ditertiarybutylphenol and compounds including 2,6-ditertiarybutylphenol groups or moieties. A non-limiting class of art-recognized UV stabilizers are hindered amine light stabilizers (HALS), such as 2,2,6,6-tetramethylpiperidine and compounds including 2,2,6,6-tetramehtylpiperidine groups or moieties. Static coloring agents include coloring agents for which the absorption spectrum thereof does not change in response to actinic radiation (such as UV and/or visible light) or the application of an electric potential, and do not include photochromic compounds and electrochromic compounds. A non-limiting class of kinetic additives includes salts, such as: alkali and alkaline earth metal salts of perchlorates, tetrafluoroborates, and hexafluorophosphates; and tetralkylammonium salts. Non-limiting examples of rheology modifies include: dialkoxyacetophenones, such as 3',4'dimethoxyacetophenone; and optionally substituted cycloalkylarylketones, such as 1-hydroxycyclohexyl phenyl ketone. Each optional additive can be present in any suitable active amount, such as from 0.05 percent by weight to 5 percent by weight, based on the total solids weight of the electrochromic layer (including the weight of the optional additive(s)).

The electrochromic layer of the electrochromic devices of the present invention can have any suitable thickness. With some embodiments, the electrochromic layer has a thickness of from 50 micrometers to 800 micrometers.

For purposes of non-limiting illustration, an electrochromic device (3) according to the present invention is depicted in FIG. 1. Electrochromic device (3) includes a first substrate (11) having a first surface (14) and a second surface (17). First surface (14) of first substrate (11) includes a first transparent electrode layer (20), which is electrically conductive. First transparent electrode layer (20) resides over at least a portion of first surface (14) of first substrate (11). With some embodiments, first transparent electrode layer (20) is in the form of one or more patterns (such as, one or more designs and/or indicia) over first surface (14) of first substrate (11). With some further embodiments, first transparent electrode layer (20) forms a substantially continuous layer over first surface (14) of first substrate (11). First transparent electrode layer (20) is, with some embodiments, in electrical contact with at least one first electrical conductor (21), which can be a first electrically conductive wire.

Electrochromic device (3) includes a second substrate (23) having a first surface (26) and a second surface (29). First surface (26) of second substrate (23) includes a second transparent electrode layer (32), which is electrically conductive. Second transparent electrode layer (32) resides over at least a portion of first surface (26) of second substrate (23). With some embodiments, second transparent electrode layer (32) is in the form of one or more patterns (such as, one or more designs and/or indicia) over first surface (26) of second substrate (23). With some further embodiments, second transparent electrode layer (32) forms a substantially continuous layer over first surface (26) of second substrate (23). Second transparent electrode layer (32) is, with some embodiments, in electrical contact with at least one second electrical conductor (33), which can be a second electrically conductive second wire.

With further reference to electrochromic device (3) of FIG. 1, first transparent electrode layer (20) and second transparent electrode layer (32) are in opposing spaced facing opposition relative to each other.

Electrochromic device (3) further includes an electrochromic layer (35) that is interposed between first transparent electrode layer (20) and second transparent electrode layer (32). With some embodiments, electrochromic layer (35) is interposed between and in abutting relationship with first transparent electrode layer (20) and second transparent electrode layer (32).

The first substrate and the second substrate of the electrochromic devices are, with some embodiments of the present invention, each independently selected from transparent substrates. Transparent substrates, from which the first and second substrates can each be independently selected, are with some embodiments, fabricated from materials including, but not limited to, silica glass, organic polymers (such as, but not limited to, polycarbonate polymers), and combinations thereof. With some embodiments, the transparent substrates, from which the first and second substrates can each be independently selected, are fabricated from materials including silica glass. The first and second substrates can each independently have any suitable thickness. With some embodiments, the first and second substrates each independently have a thickness of from 1 mm to 25 mm, or from 2 mm to 10 mm.

The first and second transparent electrode layers of the electrochromic devices of the present invention, with some embodiments, include electrically conductive inorganic oxides, electrically conductive organic materials, electrically conductive metals, and/or electrically conductive carbon, such as carbon nanotubes and/or graphene. Examples of electrically conductive inorganic oxides, include, but are not limited to: tin oxide, which can be doped with a doping material, such as indium; and zinc oxide, which can further include, for example, aluminum. Examples of electrically conductive organic materials include, but are not limited to, poly(3,4-ethylenedioxythiophene), poly(4,4-dioctyl cyclopentadithiophene), and poly(3,4-ethylenedioxythiophene):poly(styrene sulfonate). The first and second transparent electrode layers, with some embodiments, can each independently be in the form of a grid of metal wires, a grid of carbon nanotubes, and/or a layer of graphene. With some embodiments, the first and second transparent electrode layers are each independently selected from semi-transparent metal layers. With some further embodiments, one of the first and second transparent electrode layers includes (or has associated therewith) a reflective metal layer (including, for example, aluminum, gold, and/or silver) and the electrochromic device is a reflective electrochromic device, such as a controllably reflective mirror.

In accordance with some embodiments, the first and second electrode layers of the electrochromic devices of the present invention, each independently include an electrically conductive material selected from indium-tin-oxide, poly(3,4-ethylenedioxythiophene):poly(styrene sulfonate), or combinations thereof.

The first and second electrode layers of the electrochromic devices, in accordance with some embodiments of the present invention, can each independently have any suitable thickness, provided they are both transparent and electrically conductive. With some embodiments, the first and second electrode layers of the electrochromic devices of the present invention, each independently have a thickness of from 0.01 micrometers to 10 micrometers.

Examples of articles, such as articles of manufacture, that may include or be defined by the electrochromic devices of the present invention include, but are not limited to: energy efficient and/or privacy transparencies (or windows), such as architectural and transportation transparencies or windows; mirrors, such as rearview mirrors; optical filters; and ophthalmic articles, such as corrective lenses, non-corrective lenses, magnifying lenses, protective lenses, and visors; and any other article or application where variable and controllable light transmission and/or color is desired.

The present invention also relates to an electrochromic composition that includes: (i) a cathodic component having cationic charge, wherein said cathodic component further comprises counter-anions, wherein each counter-anion of said cathodic component is an anodic component having an anion covalently bonded thereto; (ii) an optional electrolyte; (iii) a polymeric thickener; and (iv) a solvent.

The cathodic component having cationic charge, the anodic component having an anion covalently bonded thereto, and the optional electrolyte are each as described previously herein with regard to the electrochromic layer of the electrochromic device of the present invention.

The cathodic component having cationic charge, with some embodiments, is present in the electrochromic composition in an amount of from 0.25 percent by weight to 6.25 percent by weight, or from 0.5 percent by weight to 5 percent by weight, or from 1 percent by weight to 3 percent by weight, the percent weights in each case being based on the total weight of the electrochromic composition.

The anodic component having an anion covalently bonded thereto is present in the electrochromic composition, with some embodiments, in an amount of from 0.25 percent by weight to 6.25 percent by weight, or from 0.5 percent by weight to 5 percent by weight, or from 1 percent by weight to 3 percent by weight, the percent weights in each case being based on the total weight of the electrochromic composition.

In accordance with some embodiments, in addition to the anodic component anion having an anion covalently bonded thereto, such as represented by Formula (I) and/or Formula (II), the anodic component of the electrochromic composition includes one or more further anodic electrochromic compounds, such as, but not limited to: ferrocene and/or ferrocene derivatives (in which at least one cyclopentadienyl ring thereof is substituted with at least one substituent, including those substituents recited previously herein); 5,10-dihydro-5,10-di(linear or branched $C_1$-$C_{10}$ alkyl)phenazine, such as 5,10-dihydro-5,10-dimethylphenazine; N-substituted phenoxazine, such as N-phenylphenoxazine; and combinations thereof. With some embodiments, the further anodic electrochromic component is present in an amount of 1 percent by weight to 50 percent by weight, of from 1 percent by weight to 25 percent by weight, or from 1 percent by weight to 10 percent by weight, or from 1 percent by weight to 5 percent by weight, the percent weights each being based on the total weight of the anodic component anion and the further anodic electrochromic component. In accordance with some embodiments, when a further anodic component in present (in addition to the anodic component anion having an anion covalently bonded thereto) a further cathodic component (or further appropriate amount of cathodic component) can also be present. The further cathodic component, with some embodiments, comprises one or more cathodic components represented by Formulas (III) and/or (IV).

The electrolyte is present in the electrochromic composition, with some embodiments, in an amount of from 1 percent by weight to 75 percent by weight, or from 5 percent by weight to 50 percent by weight, or from 10 percent by weight to 30 percent by weight, the percent weights in each case being based on the total weight of the electrochromic composition.

The polymeric thickener of the electrochromic composition of the electrochromic composition includes, with some embodiments, a polymer, where the polymer includes at least one of poly((meth)acrylonitrile), poly(vinylidene fluoride), poly(vinylidene fluoride-co-perfluoro(linear or branched $C_1$-$C_6$ alkylene)), or poly((linear or branched $C_1$-$C_8$ alkyl)(meth)acrylate).

The polymeric thickener is present in the electrochromic composition, with some embodiments, in an amount of from 5 percent by weight to 80 percent by weight, or from 10 percent by weight to 60 percent by weight, or from 15 percent by weight to 50 percent by weight, the percent weights in each case being based on the total weight of the electrochromic composition.

The electrochromic composition of the present invention includes a solvent. With some embodiments, the solvent of the electrochromic composition includes at least one of ethylene carbonate, propylene carbonate, gamma-butyrolactone, gamma-valerolactone, N-methylpyrrolidone, polyethylene glycol, carboxylic acid esters of polyethylene glycol, sulfolane, alpha, omega-($C_2$-$C_8$)dinitriles, or di(linear or branched $C_1$-$C_8$)acetamides.

The solvent is present in the electrochromic composition, with some embodiments, in and amount of from 10 to 75 percent by weight, or from 20 to 60 percent by weight, or from 25 percent by weight to 50 percent by weight, the percent weights in each case being based on the total weight of the electrochromic composition.

The electrochromic composition of the present invention can, with some embodiments, include one or more art-recognized optional additives, such as, but not limited to, thermal stabilizers, UV stabilizers, rheology modifiers, static coloring agents (such as static tints and/or static dyes), kinetic additives (that accelerate electrode reaction) and combinations thereof. The optional additives are in each case as described previously herein with regard to the electrochromic device of the present invention. Each optional additive can be present in the electrochromic composition in any suitable active amount, such as from 0.05 percent by weight to 5 percent by weight, based on the total weight of the electrochromic composition (including the weight of the optional additive(s)).

In accordance with some embodiments of the present invention, the electrochromic layer of the electrochromic device is formed from the electrochromic composition of the present invention. In accordance with some embodiments of the present invention, formation of the electrochromic composition and electrochromic layer includes the following steps. First, all components of the electrochromic composition, other than the polymeric thickener, are mixed under sheer (such as with an impeller) until a homogenous mixture is formed. Secondly, the polymeric thickener is added, and the combination is subjected to homogenization, which results in the formation of a thick slurry. A liquid film of the thick slurry is formed, such as using a doctor blade or draw-down bar, on a sacrificial or temporary liner (composed of polyethylene terephthalate, in some embodiments). The liquid film while on the sacrificial/temporary liner is subjected to elevated temperature, such as from 60° to 90° C. for 3 to 10 minutes, which results in the formation of a solidified film/layer, which is the electrochromic layer. The solidified film/electrochromic layer, is separated from the sacrificial/temporary liner (which is discarded), cut to size (if necessary), and placed over or onto a first transparent electrode layer of a first substrate. The second transparent electrode of a second substrate is positioned over or onto the other (or facing/exposed) side of the electrochromic layer, to form a stack that includes the first substrate, the first transparent electrode, the electrochromic layer, the second transparent electrode, and the second substrate. The stack may further include electrical connectors that are in separate electrical contact with the first and second transparent electrodes. The stack (with an optional gasket surrounding the outer edges of at least the electrochromic layer) is subjected to vacuum lamination, with the concurrent application of elevated temperature, such as from 110° C. to 200° C., for a period of time, such as from 10 to 30 minutes. After cooling, the so formed electrochromic device is removed from vacuum lamination device.

The present invention can further be characterized by one or more of the following non-limiting clauses.

Clause 1: An electrochromic device comprising:

(a) a first substrate having a surface comprising a first transparent electrode layer;

(b) a second substrate having a surface comprising a second transparent conductive electrode layer, wherein said first transparent electrode layer and said second transparent electrode layer are in opposing spaced opposition; and (c) an electrochromic layer interposed between said first transparent electrically conductive electrode layer and said second transparent electrically conductive electrode layer, wherein said electrochromic layer comprises, (i) an electrochromic material comprising a cathodic component having cationic charge, wherein said cathodic component further comprises counter-anions, wherein each counter-anion of said cathodic component is an anodic component having an anion covalently bonded thereto, (ii) an optional electrolyte, and (iii) a polymer matrix.

Clause 2: The electrochromic device of clause 1, wherein said cathodic component having cationic charge and said anodic component having said anion covalently bonded thereto, together have a net neutral charge.

Clause 3: The electrochromic device of clause 1 or clause 2, wherein said anodic component having an anion covalently bonded thereto is selected from an anodic component represented by at least one of the following Formula (I) or Formula (II), (I)

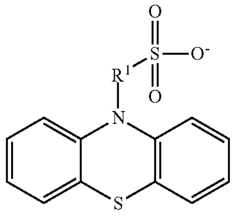

(II)

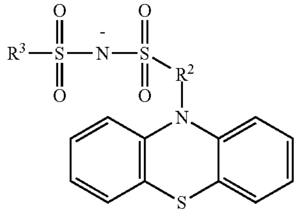

wherein for Formula (I), $R^1$ is selected from divalent linear or branched alkane linking group, and for Formula (II), $R^2$ is selected from divalent linear or branched alkane linking group, and $R^3$ is selected from fluorine, linear or branched fluorinated alkyl, or linear or branched perfluorinated alkyl.

Clause 4: The electrochromic device of clause 3, wherein for Formula (I), $R^1$ is selected from divalent linear or branched $C_1$-$C_{10}$ alkane linking group, and for Formula (II), $R^2$ is selected from divalent linear or branched $C_1$-$C_{10}$ alkane linking group, and $R^3$ is selected from fluorine, linear or branched $C_1$-$C_{10}$ fluorinated alkyl, or linear or branched $C_1$-$C_{10}$ perfluorinated alkyl.

Clause 5: The electrochromic device of clause 3 or clause 4, wherein for Formula (I) $R^1$ is selected from divalent linear or branched $C_1$-$C_5$ alkane linking group, and for Formula (II), $R^2$ is selected from divalent linear or branched $C_1$-$C_5$ alkyl, and $R^3$ is selected from linear or branched $C_1$-$C_5$ perfluorinated alkyl.

Clause 6: The electrochromic device of any one of clauses 1, 2, 3, 4, or 5, wherein said cathodic component comprises at least one of a 1,1'-disubstituted-4,4'-dipyridinium cation represented by the following Formula (III), or a 1,1-(alkane-alpha, omega-diyl)-bis-(1'-substituted-4,4'-dipyridinium) cation represented by the following Formula (VI), Formula (III)

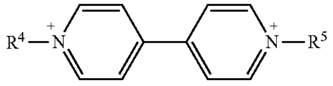

Formula (IV)

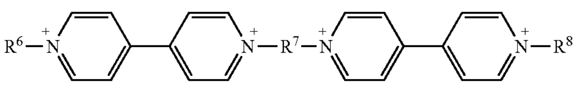

wherein for Formula (III), $R^4$ and $R^5$ are each independently selected from linear or branched $C_1$-$C_{10}$ alkyl, unsubstituted $C_3$-$C_7$ cycloalkyl, substituted $C_3$-$C_7$ cycloalkyl, unsubstituted aryl, and substituted aryl, and for Formula (IV), $R^6$ and $R^8$ are each independently selected from linear or branched $C_1$-$C_{10}$ alkyl, unsubstituted $C_3$-$C_7$ cycloalkyl, substituted $C_3$-$C_7$ cycloalkyl, unsubstituted aryl, and substituted aryl, and $R^7$ is selected from divalent linear or branched $C_1$-$C_{10}$ alkane linking group.

Clause 7: The electrochromic device of clause 6, wherein for Formula (III) $R^4$ and $R^5$ are each independently selected from linear or branched $C_1$-$C_4$ alkyl, unsubstituted phenyl, and substituted phenyl, and for Formula (IV) $R^6$ and $R^8$ are each independently selected from linear or branched $C_1$-$C_4$ alkyl, unsubstituted phenyl, and substituted phenyl, and $R^7$ is selected from divalent linear or branched $C_1$-$C_8$ alkane linking group.

Clause 8: The electrochromic device of any one of clauses 1, 2, 3, 4, 5, 6, or 7, wherein said electrolyte is present and comprises, at least one electrolyte anion, wherein each electrolyte anion is independently selected from bis(perfluoro(linear or branched $C_1$-$C_6$ alkysulfonyl)imide, and at least one electrolyte cation, wherein each electrolyte cation is independently selected from 1-(linear or branched $C_1$-$C_6$ alkyl)-3-(linear or branched $C_1$-$C_6$ alkyl)imidazolium, 1-(linear or branched $C_1$-$C_6$ alkyl)-1-(linear or branched $C_1$-$C_6$ alkyl)pyrrolidinium, 1-(linear or branched $C_1$-$C_6$ alkyl)-1-(linear or branched $C_1$-$C_6$ alkyl)piperidinium, phosphonium cations, such as, but not limited to tetra(linear or branched $C_1$-$C_6$ alkyl)phosphonium, or tri($C_5$-$C_8$ cycloalkyl)-(linear or branched $C_1$-$C_6$ alkyl)phosphonium, or ammonium cations, such as, but not limited to, tetra(linear or branched $C_1$-$C_6$)ammonium, and tri($C_5$-$C_8$ cycloalkyl)-(linear or branched $C_1$-$C_6$ alkyl)ammonium.

Clause 9: The electrochromic device of any one of clauses 1, 2, 3, 4, 5, 6, 7, or 8, wherein said polymer matrix comprises a polymer, wherein said polymer comprises at least one of poly((meth)acrylonitrile), poly(vinylidene fluoride), poly(vinylidene fluoride-co-perfluoro(linear or branched $C_1$-$C_6$ alkylene)), or poly((linear or branched $C_1$-$C_8$ alkyl)(meth)acrylate).

Clause 10: An article of manufacture comprising said electrochromic device of any one of clauses 1, 2, 3, 4, 5, 6, 7, 8, or 9, wherein said article of manufacture is selected from, energy efficient transparencies, privacy transparencies, mirrors, optical filters, or ophthalmic articles.

Clause 11: An electrochromic composition comprising, (i) a cathodic component having cationic charge, wherein said cathodic component further comprises counter-anions, wherein each counter-anion of said cathodic component is an anodic component having an anion covalently bonded thereto, (ii) an optional electrolyte, (iii) a polymeric thickener, and (iv) a solvent.

Clause 12: The electrochromic composition of clause 11, wherein said cathodic component having cationic charge and said anodic component having said anion covalently bonded thereto, together have a net neutral charge.

Clause 13: The electrochromic composition of clause 11 or clause 12, wherein said anodic component having an anion covalently bonded thereto is selected from an anodic component represented by at least one of the following Formula (I) or Formula (II), (I)

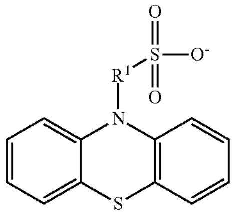

(II)

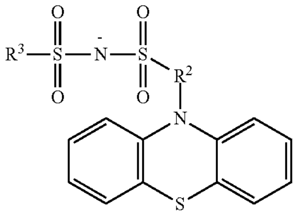

wherein for Formula (I), $R^1$ is selected from divalent linear or branched alkane linking group, and for Formula (II), $R^2$ is selected from divalent linear or branched alkane linking group, and $R^3$ is selected from fluorine, linear or branched fluorinated alkyl, or linear or branched perfluorinated alkyl.

Clause 14: The electrochromic composition of clause 13, wherein for Formula (I), $R^1$ is selected from divalent linear or branched $C_1$-$C_{10}$ alkane linking group, and for Formula (II), $R^2$ is selected from divalent linear or branched $C_1$-$C_{10}$ alkane linking group, and $R^3$ is selected from fluorine, linear or branched $C_1$-$C_{10}$ fluorinated alkyl, or linear or branched $C_1$-$C_{10}$ perfluorinated alkyl.

Clause 15: The electrochromic composition of clause 12 or clause 13, wherein for Formula (I), $R^1$ is selected from divalent linear or branched $C_1$-$C_5$ alkane linking group, and for Formula (II), $R^2$ is selected from divalent linear or branched $C_1$-$C_5$ alkyl, and $R^3$ is selected from linear or branched $C_1$-$C_5$ perfluorinated alkyl.

Clause 16: The electrochromic composition of any one of clauses 11, 12, 13, 14, or 15, wherein said cathodic component comprises at least one of a 1,1'-disubstituted-4,4'-dipyridinium cation represented by the following Formula (III), or a 1,1-(alkane-alpha, omega-diyl)-bis-(1'-substituted-4,4'-dipyridinium) cation represented by the following Formula (VI), Formula (III)

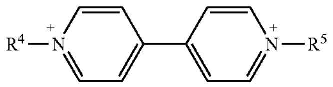

Formula (IV)

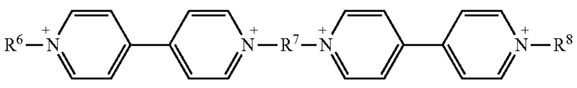

wherein for Formula (III), $R^4$ and $R^5$ are each independently selected from linear or branched $C_1$-$C_{10}$ alkyl, unsubstituted $C_3$-$C_7$ cycloalkyl, substituted $C_3$-$C_7$ cycloalkyl, unsubstituted aryl, and substituted aryl, and for Formula (IV), $R^6$ and $R^8$ are each independently selected from linear or branched $C_1$-$C_{10}$ alkyl, unsubstituted $C_3$-$C_7$ cycloalkyl, substituted $C_3$-$C_7$ cycloalkyl, unsubstituted aryl, and substituted aryl, and $R^7$ is selected from divalent linear or branched $C_1$-$C_{10}$ alkane linking group.

Clause 17: The electrochromic composition of clause 16, wherein for Formula (III) $R^4$ and $R^5$ are each independently selected from linear or branched $C_1$-$C_4$ alkyl, unsubstituted phenyl, and substituted phenyl, and for Formula (IV) $R^6$ and $R^8$ are each independently selected from linear or branched $C_1$-$C_4$ alkyl, unsubstituted phenyl, and substituted phenyl, and $R^7$ is selected from divalent linear or branched $C_1$-$C_8$ alkane linking group.

Clause 18: The electrochromic composition of any one of clauses 11, 12, 13, 14, 15, 16, or 17, wherein said electrolyte is present and comprises, at least one electrolyte anion, wherein each electrolyte anion is independently selected from bis(perfluoro(linear or branched $C_1$-$C_6$ alkysulfonyl)imide, and at least one electrolyte cation, wherein each electrolyte cation is independently selected from 1-(linear or branched $C_1$-$C_6$ alkyl)-3-(linear or branched $C_1$-$C_6$ alkyl)imidazolium, 1-(linear or branched $C_1$-$C_6$ alkyl)-1-(linear or branched $C_1$-$C_6$ alkyl)pyrrolidinium, 1-(linear or branched $C_1$-$C_6$ alkyl)-1-(linear or branched $C_1$-$C_6$ alkyl)piperidinium, 1-(linear or branched $C_1$-$C_6$ alkyl)-1-(linear or branched $C_1$-$C_6$ alkyl)piperidinium, phosphonium cations, such as, but not limited to tetra(linear or branched $C_1$-$C_6$ alkyl)phosphonium, or tri($C_5$-$C_8$ cycloalkyl)-(linear or branched $C_1$-$C_6$ alkyl)phosphonium, or ammonium cations, such as, but not limited to, tetra(linear or branched $C_1$-$C_6$)ammonium, or tri($C_5$-$C_8$ cycloalkyl)-(linear or branched $C_1$-$C_6$ alkyl)ammonium.

Clause 19: The electrochromic composition of any one of clause 11, 12, 13, 14, 15, 16, 17, or 18, wherein said polymeric thickener comprises a polymer, wherein said polymer comprises at least one of poly((meth)acrylonitrile), poly(vinylidene fluoride), poly(vinylidene fluoride-co-perfluoro(linear or branched $C_1$-$C_6$ alkylene)), or poly((linear or branched $C_1$-$C_8$ alkyl)(meth)acrylate).

Clause 20: The electrochromic composition of any one of clauses 11, 12, 13, 14, 15, 16, 17, 18, or 19, wherein said solvent comprises at least one of ethylene carbonate, propylene carbonate, gamma-butyrolactone, gamma-valerolactone, N-methylpyrrolidone, polyethylene glycol, carboxylic acid esters of polyethylene glycol, sulfolane, alpha, omega-($C_2$-$C_8$)dinitriles, or di(linear or branched $C_1$-$C_8$)acetamides.

The present invention is more particularly described in the following examples, which are intended as illustrative only, since numerous modifications and variations therein will be apparent to those skilled in the art.

EXAMPLES

In Part-1 of the examples there is described the synthesis of anodic components having an anion covalently bonded thereto, according to the present invention. In Part-2, there is described the synthesis of a cathodic component having cationic charge where each counter-anion thereof is an anodic component having an anion covalently bonded thereto, according to the present invention. In Part-3, there is described the preparation of an electrochromic device according to the present invention. In Part-4, testing of the electrochromic device according to the present invention of Part-3, is described.

Part-1

Synthesis Example 1

With reference to Scheme-(1) below, there is provided a non-limiting description of the preparation of an anodic component having an anion covalently bonded thereto according to the present invention represented by Formula (I), where $R^1$ is a divalent n-propane linking group.

Into an oven dried 3-neck, 500 ml round bottomed flask with magnetic stirring was added 200 mL of dimethylformamide (DMF) and 10 g of (1) phenothiazine (50.2 mmol). The solution was stirred while being purge with nitrogen for 1 hour. To the reaction mixture was added 2.4 g of 60% NaH (60 mmol). The solution was observed to turn deep red as bubbles were produced therefrom. After continuous mixing under nitrogen for one hour, the production of bubbles was observed to cease. While under a nitrogen sweep is 6.6 g of (2) 1,3-propanesultone (55.2 mmol) dissolved in 10 g of dry DMF, was added drop-wise to the contents of the flask. After completion of the addition of (2) 1,3-propanesultone, the reaction mixture was left to stir at room temperature for 18 hours under nitrogen.

The reaction was quenched by the addition of 100 mL of deionized (DI) water and the solvent was removed by the application of vacuum, after which an oily substance remained in the flask. To the oily substance was added 50 mL of ethyl acetate, which resulted in the formation of a precipitate that was collected by vacuum filtration. The precipitate was washed with cold ethyl acetate and dried overnight under vacuum at 60° C. to yield the desired product (3) sodium 3-(10H-phenothiazin-10-yl)-propane-1-sulfonate, as an off-white solid.

Scheme-(1)

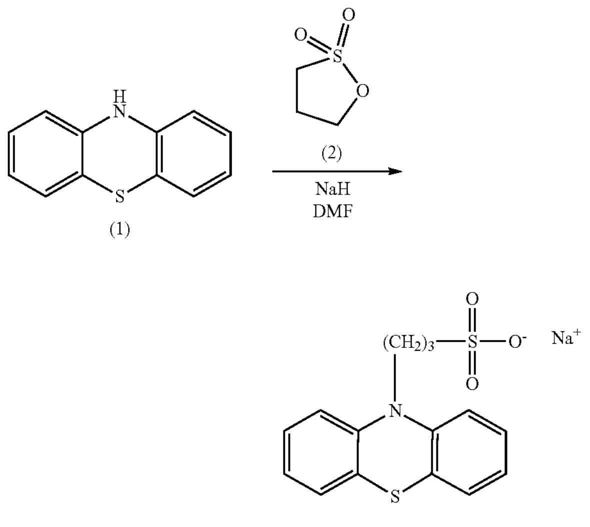

(3)

Synthesis Example 2

With reference to Scheme-(2) below, there is provided a non-limiting description of the preparation of an anodic component having an anion covalently bonded thereto according to the present invention represented by Formula (II), where $R^2$ is a divalent n-propane linking group, and $R^3$ is trifluoromethyl.

The (3) sodium 3-(10H-phenothiazin-10-yl)-propane-1-sulfonate was prepared in accordance with Synthesis Example 1. One gram (0.0029 mol) of (3) sodium 3-(10H-phenothiazin-10-yl)propane-1-sulfonate was fine ground with mortar and pestle, and then placed in a 100 ml round-bottom flask equipped with a magnetic stir bar and a reflux condenser with a $N_2$ sweep/blanket. Acetone in an amount of 20 ml and 40 mg of 18-crown-6 ether were added to the flask and the mixture was stirred vigorously for 15 minutes. The solution turned cloudy, but solid sodium salt (3) was observed to be present. (4) Cyanuric chloride (540 mg, 0.0029 mol, 1 equiv.) was added under vigorous stirring under $N_2$. The mixture was refluxed for 24 hours on an oil bath (at about 80° C.). The color of the solution turned orange and a fine precipitate formed. Large chunks of initial Na salt (3) were no longer observable. Thin layer chromatography (TLC) showed the presence of a single reaction product that turned pink upon exposure to short-wave (316 nm) UV in air, evidencing formation of (5) 3-(10H-phenothiazin-10-yl)-propane-1-sulfonyl chloride. The product (5) was fairly mobile in 50:50 EtOAc/Hexanes. The reaction mixture was cooled to room temperature and filtered through a thin layer of alumina. The solvent was removed under vacuum to give 1.25 g of orange-yellow glassy solid (5). The product (5) was dissolved in MeCN and the solids were filtered off. The filtrate was used in the next step without additional purification.

(6) Trifluoromethylsulfonamide (4.53 g, 0.0305 mol, 1.05 equiv.) and potassium carbonate (40 g, 0.29 mol, 10 equiv.) were placed in a 500 ml 3-neck flask equipped with a reflux condenser, magnetic stir bar and a fritted Schlenk funnel. Nitrogen feeds were attached to the condenser and the Schlenk funnel and secured with plastic clips. An intense nitrogen flux was used to flush the vessel for 15 seconds, and a septum was installed in the remaining neck. Anhydrous MeCN in an amount of 100 ml was added through the septum using a syringe. The mixture was vigorously stirred for 20 minutes, yielding a white hazy dispersion. To the crude (5) 3-(10H-phenothiazin-10-yl)propane-1-sulfonyl chloride (9.84 g, 0.029 mol) (filtrate of the preceding step) was added 50 ml dry MeCN under nitrogen flux, and the resulting solution was transferred to the fritted Schlenk funnel. The Schlenk funnel was purged with nitrogen and plugged with a stopper secured with a clip. The solution of MeCN and (5) 3-(10H-phenothiazin-10-yl)propane-1-sulfonyl chloride was added dropwise to the 3-neck flask over a period of one hour at room temperature. The contents of the 3-neck flask were refluxed for 24 hours. Formation of bulky precipitate was observed. The precipitate was filtered off and the resulting solution was concentrated under vacuum. The residue was recrystallized from water to yield the product (7) potassium 3-(10H-phenothiazin-10-yl)-N-((trifluoromethyl)sulfonyl)propane-1-sulfonamide, in the form of brown needles.

Scheme-(2)

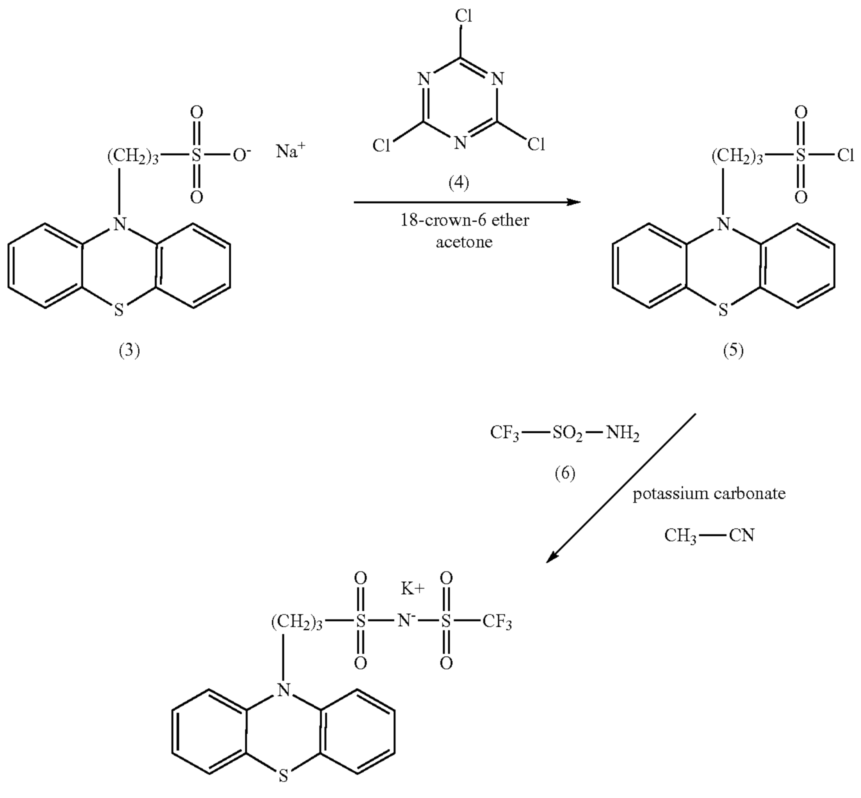

(3) (4) (5) (6) (7)

Part-2

With reference to Scheme-(3) below, there is provided a non-limiting description of the preparation of a cathodic component according to the present invention, (9) 1,1'-diheptyl-[4,4'-bypyridine]-1,1'-diium-bis-[3-(10H-phenothiazin-10-yl)propane-1-sulfonate. With further reference to the following Scheme-(3), for compounds (8) and (9), $R^4$ and $R^5$ are in each case heptyl.

Into a 200 mL Erlenmeyer flask with magnetic stirring was added 2 g of (8) 1,1'-diheptyl-[4,4'-bipyridine]-1,1'-diium dibromide (3.89 mmol) and 50 mL of deionized (DI) water. The mixture was stirred until a solution was formed. While still stirring, a solution of 2.8 g of (3) sodium 3-(10H-phenothiazin-10-yl)-propane-1-sulfonate (8.16 mmol/2.1 eq) in 50 mL of water was added thereto. A dark purple precipitate was promptly formed. The reaction mixture was stirred for 3 hours. The precipitate was collected via vacuum filtration and washed several times with water and dried overnight under vacuum at 60° C. to yield the product (9) 1,1'-diheptyl-[4,4'-bypyridine]-1,1'-diium-bis-[3-(10H-phenothiazin-10-yl)propane-1-sulfonate, in the form of dark purple crystals.

Scheme-(3)

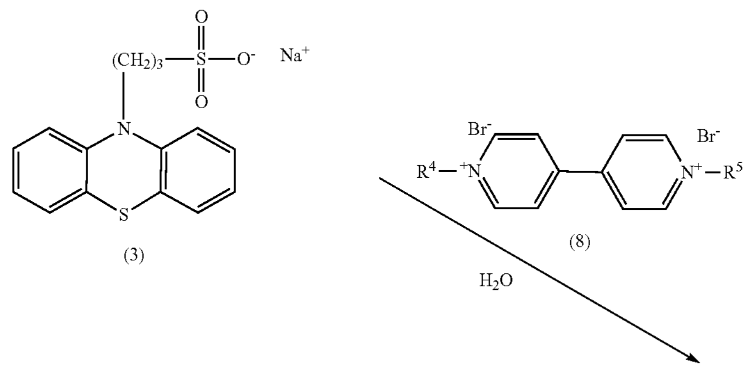

2 (3) (8)

-continued

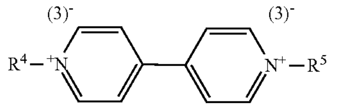

\+ 2 NaBr (9)

Part-3

An electrochromic device according to the present invention was prepared in accordance with the following description. An initial solution was prepared from the following components, with magnetic stirring: propylene carbonate (7 g); ethylene carbonate (3 g); 1-ethyl-3-methylimidazolium bis(trifluoromethane)sulfonimide (EMIM-TFSI) (1 g); and 1,1'-diheptyl-[4,4'-bypyridine]-1,1'-diium-bis-[3-(10H-phenothiazin-10-yl)propane-1-sulfonate (PT2V) (200 mg). To the initial solution was added 3.5 g of polyacrylonitrile, followed by homogenization of the combination, which resulted in the formation of a thick slurry. A liquid film of the thick slurry was formed using doctor blade on a sacrificial polyethylene terephthalate (PET) liner to a thickness of 400 micrometers (um). The liquid film was heated to 70° C. for 10 minutes, which resulted in the formation of a solidified film/layer, which was the electrochromic layer. The solidified film/electrochromic layer, was separated from the sacrificial/temporary liner, cut to size (2"×3"; 5.08 cm×7.62 cm), and placed onto a fluorine doped tin oxide (FTO)-glass electrode (3"×4"; 7.62 cm×10.16 cm) that already had copper tape wrapped over the edge, which was covered with insulating polyimide. A prefabricated thermoplastic gasket of 0.5" (1.27 cm) in width and 400 microns in thickness was added, which surrounded the active area. A second fluorine doped tin oxide (FTO)-glass electrode was positioned over of the electrochromic layer. The stack was subjected to vacuum lamination at 140° C. for 15 minutes to fully melt and seal the gasket. After cooling, the so formed electrochromic device was removed from vacuum lamination device.

Part-4

Figure 2:
FIG. 2 is a photographic representation of an electrochromic device according to the present invention, as described in Part-3 of the Examples, in a clear/unactivated state (a) on the left, and a dark/activated state (b) on the right.

The electrochromic device of Part-3 was placed over (in front of) a light colored label including indicia (Vitro® Architectural Glass), and was subjected to an electric potential of 1.2 V for 10 minutes. With reference to FIG. 2 of the drawings, a photographic representation of the electrochromic device of Part-3 in a clear/unactivated state is depicted on the left (a). With further reference to FIG. 2, a photographic representation of the electrochromic device of Part-3 in a darkened/activated state (after being subjected to 1.2 V for 10 minutes) is depicted on the left (b). As depicted in FIG. 2, electrochromic devices according to the present invention are capable of providing a significant and desirable change in visual light transmission (VLT) in the darkened/activated state.

The present invention has been described with reference to specific details of particular embodiments thereof. It is not intended that such details be regarded as limitations upon the scope of the invention except insofar as to the extent that they are included in the accompanying claims.

What is claimed is:

1. An electrochromic device comprising:

(a) a first substrate having a surface comprising a first transparent electrode layer;

(b) a second substrate having a surface comprising a second transparent conductive electrode layer, wherein said first transparent electrode layer and said second transparent electrode layer are in opposing spaced opposition; and (c) an electrochromic layer interposed between said first transparent electrically conductive electrode layer and said second transparent electrically conductive electrode layer, wherein said electrochromic layer comprises, (i) an electrochromic material comprising a cathodic component having cationic charge, wherein said cathodic component further comprises counter-anions, wherein each counter-anion of said cathodic component is an anodic component having an anion covalently bonded thereto, (ii) an optional electrolyte, and (iii) a polymer matrix, wherein said anodic component having an anion covalently bonded thereto is selected from an anodic component represented by at least one of the following Formula (I) or Formula (II), (I)

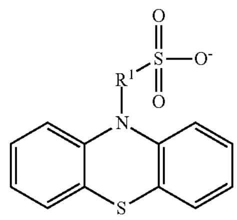

(II)

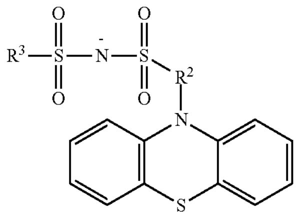

wherein for Formula (I), $R^1$ is selected from divalent linear or branched alkane linking group, and for Formula (II), $R^2$ is selected from divalent linear or branched alkane linking group, and $R^3$ is selected from fluorine, linear or branched fluorinated alkyl, or linear or branched perfluorinated alkyl.

2. The electrochromic device of claim 1, wherein said cathodic component having cationic charge and said anodic component having said anion covalently bonded thereto, together have a net neutral charge.

3. The electrochromic device of claim 1, wherein for Formula (I), $R^1$ is selected from divalent linear or branched $C_1$-$C_{10}$ alkane linking group, and for Formula (II), $R^2$ is selected from divalent linear or branched $C_1$-$C_{10}$ alkane linking group, and $R^3$ is selected from fluorine, linear or branched $C_1$-$C_{10}$ fluorinated alkyl, or linear or branched $C_1$-$C_{10}$ perfluorinated alkyl.

4. The electrochromic device of claim 3, wherein for Formula (I) $R^1$ is selected from divalent linear or branched $C_1$-$C_5$ alkane linking group, and for Formula (II), $R^2$ is selected from divalent linear or branched $C_1$-$C_5$ alkyl, and $R^3$ is selected from linear or branched $C_1$-$C_5$ perfluorinated alkyl.

5. The electrochromic device of claim 1, wherein said cathodic component comprises at least one of a 1,1'-disubstituted-4,4'-dipyridinium cation represented by the following Formula (III), or a 1,1-(alkane-alpha, omega-diyl)-bis-(1'-substituted-4,4'-dipyridinium) cation represented by the following Formula (VI), Formula (III)

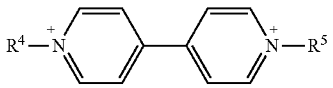

Formula (IV)

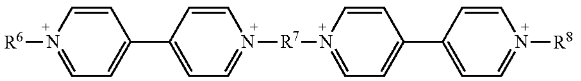

wherein for Formula (III), $R^4$ and $R^5$ are each independently selected from linear or branched $C_1$-$C_{10}$ alkyl, unsubstituted $C_3$-$C_7$ cycloalkyl, substituted $C_3$-$C_7$ cycloalkyl, unsubstituted aryl, and substituted aryl, and for Formula (IV), $R^6$ and $R^8$ are each independently selected from linear or branched $C_1$-$C_{10}$ alkyl, unsubstituted $C_3$-$C_7$ cycloalkyl, substituted $C_3$-$C_7$ cycloalkyl, unsubstituted aryl, and substituted aryl, and $R^7$ is selected from divalent linear or branched $C_1$-$C_{10}$ alkane linking group.

6. The electrochromic device of claim 5, wherein for Formula (III) $R^4$ and $R^5$ are each independently selected from linear or branched $C_1$-$C_4$ alkyl, unsubstituted phenyl, and substituted phenyl, and for Formula (IV) $R^6$ and $R^8$ are each independently selected from linear or branched $C_1$-$C_4$ alkyl, unsubstituted phenyl, and substituted phenyl, and $R^7$ is selected from divalent linear or branched $C_1$-$C_8$ alkane linking group.

7. The electrochromic device of claim 1, wherein said electrolyte is present and comprises, at least one electrolyte anion, wherein each electrolyte anion is independently selected from bis(perfluoro(linear or branched $C_1$-$C_6$ alkysulfonyl)imide, and at least one electrolyte cation, wherein each electrolyte cation is independently selected from 1-(linear or branched $C_1$-$C_6$ alkyl)-3-(linear or branched $C_1$-$C_6$ alkyl)imidazolium, 1-(linear or branched $C_1$-$C_6$ alkyl)-1-(linear or branched $C_1$-$C_6$ alkyl)pyrrolidinium, 1-(linear or branched $C_1$-$C_6$ alkyl)-1-(linear or branched $C_1$-$C_6$ alkyl)piperidinium, tetra(linear or branched $C_1$-$C_6$ alkyl)phosphonium, tri($C_5$-$C_8$ cycloalkyl)-(linear or branched $C_1$-$C_6$ alkyl)phosphonium, tetra(linear or branched $C_1$-$C_6$)ammonium, or tri($C_5$-$C_8$ cycloalkyl)-(linear or branched $C_1$-$C_6$ alkyl)ammonium.

8. The electrochromic device of claim 1, wherein said polymer matrix comprises a polymer, wherein said polymer comprises at least one of poly((meth)acrylonitrile), poly(vinylidene fluoride), poly(vinylidene fluoride-co-perfluoro(linear or branched $C_1$-$C_6$ alkylene)), or poly((linear or branched $C_1$-$C_8$ alkyl)(meth)acrylate).

9. An electrochromic composition comprising, (i) a cathodic component having cationic charge, wherein said cathodic component further comprises counter-anions, wherein each counter-anion of said cathodic component is an anodic component having an anion covalently bonded thereto, (ii) an optional electrolyte, (iii) a polymeric thickener, and (iv) a solvent, wherein said anodic component having an anion covalently bonded thereto is selected from an anodic component represented by at least one of the following Formula (I) or Formula (II), (I)

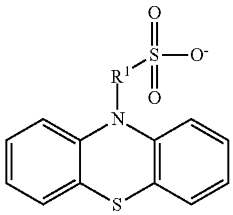

(II)

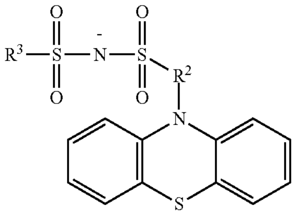

wherein for Formula (I), $R^1$ is selected from divalent linear or branched alkane linking group, and for Formula (II), $R^2$ is selected from divalent linear or branched alkane linking group, and $R^3$ is selected from fluorine, linear or branched fluorinated alkyl, or linear or branched perfluorinated alkyl.

10. The electrochromic composition of claim 9, wherein said cathodic component having cationic charge and said anodic component having said anion covalently bonded thereto, together have a net neutral charge.

11. The electrochromic composition of claim 9, wherein for Formula (I), $R^1$ is selected from divalent linear or branched $C_1$-$C_{10}$ alkane linking group, and for Formula (II), $R^2$ is selected from divalent linear or branched $C_1$-$C_{10}$ alkane linking group, and $R^3$ is selected from fluorine, linear or branched $C_1$-$C_{10}$ fluorinated alkyl, or linear or branched $C_1$-$C_{10}$ perfluorinated alkyl.

12. The electrochromic composition of claim 11, wherein for Formula (I), $R^1$ is selected from divalent linear or branched $C_1$-$C_5$ alkane linking group, and for Formula (II), $R^2$ is selected from divalent linear or branched $C_1$-$C_5$ alkyl, and $R^3$ is selected from linear or branched $C_1$-$C_5$ perfluorinated alkyl.

13. The electrochromic composition of claim 9, wherein said cathodic component comprises at least one of a 1,1'-disubstituted-4,4'-dipyridinium cation represented by the following Formula (III), or a 1,1-(alkane-alpha, omega-diyl)-bis-(1'-substituted-4,4'-dipyridinium) cation represented by the following Formula (VI), Formula (III)

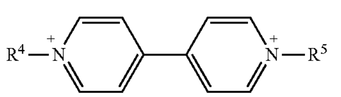

Formula (IV)

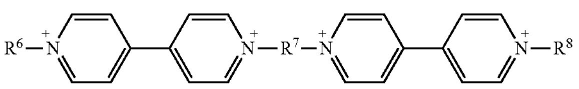

wherein for Formula (III), $R^4$ and $R^5$ are each independently selected from linear or branched $C_1$-$C_{10}$ alkyl, unsubstituted $C_3$-$C_7$ cycloalkyl, substituted $C_3$-$C_7$ cycloalkyl, unsubstituted aryl, and substituted aryl, and for Formula (IV), $R^6$ and $R^8$ are each independently selected from linear or branched $C_1$-$C_{10}$ alkyl, unsubstituted $C_3$-$C_7$ cycloalkyl, substituted $C_3$-$C_7$ cycloalkyl, unsubstituted aryl, and substituted aryl, and $R^7$ is selected from divalent linear or branched $C_1$-$C_{10}$ alkane linking group.

14. The electrochromic composition of claim 13, wherein for Formula (III) $R^4$ and $R^5$ are each independently selected from linear or branched $C_1$-$C_4$ alkyl, unsubstituted phenyl, and substituted phenyl, and for Formula (IV) $R^6$ and $R^8$ are each independently selected from linear or branched $C_1$-$C_4$ alkyl, unsubstituted phenyl, and substituted phenyl, and $R^7$ is selected from divalent linear or branched $C_1$-$C_8$ alkane linking group.

15. The electrochromic composition of claim 9, wherein said electrolyte is present and comprises, at least one electrolyte anion, wherein each electrolyte anion is independently selected from bis(perfluoro(linear or branched $C_1$-$C_6$ alkysulfonyl)imide, and at least one electrolyte cation, wherein each electrolyte cation is independently selected from 1-(linear or branched $C_1$-$C_6$ alkyl)-3-(linear or branched $C_1$-$C_6$ alkyl)imidazolium, 1-(linear or branched $C_1$-$C_6$ alkyl)-1-(linear or branched $C_1$-$C_6$ alkyl)pyrrolidinium, 1-(linear or branched $C_1$-$C_6$ alkyl)-1-(linear or branched $C_1$-$C_6$ alkyl)piperidinium, tetra(linear or branched $C_1$-$C_6$ alkyl)phosphonium, tri($C_5$-$C_8$ cycloalkyl)-(linear or branched $C_1$-$C_6$ alkyl)phosphonium, tetra(linear or branched $C_1$-$C_6$)ammonium, or tri($C_5$-$C_8$ cycloalkyl)-(linear or branched $C_1$-$C_6$ alkyl)ammonium.

16. The electrochromic composition of claim 9, wherein said polymeric thickener comprises a polymer, wherein said polymer comprises at least one of poly((meth)acrylonitrile), poly(vinylidene fluoride), poly(vinylidene fluoride-co-perfluoro(linear or branched $C_1$-$C_6$ alkylene)), or poly((linear or branched $C_1$-$C_8$ alkyl)(meth)acrylate).

17. The electrochromic composition of claim 9, wherein said solvent comprises at least one of ethylene carbonate, propylene carbonate, gamma-butyrolactone, gamma-valerolactone, N-methylpyrrolidone, polyethylene glycol, carboxylic acid esters of polyethylene glycol, sulfolane, alpha, omega-($C_2$-$C_8$)dinitriles, or di(linear or branched $C_1$-$C_8$) acetamides.

* * * * *